United States Patent [19]

Scoggin

[11] 4,075,287
[45] Feb. 21, 1978

[54] SEPARATION PROCESS

[75] Inventor: Jack S. Scoggin, Bartlesville, Okla.

[73] Assignee: Phillips Petroleum Company, Bartlesville, Okla.

[21] Appl. No.: 735,911

[22] Filed: Oct. 27, 1976

[51] Int. Cl.$^2$ .................. C08F 297/08; C08F 6/00; B01D 3/00; B01D 3/10

[52] U.S. Cl. .................. 260/878 B; 203/39; 203/77; 526/68; 526/77

[58] Field of Search .................. 203/39, 77; 526/68, 526/77; 260/878 B

[56] References Cited

U.S. PATENT DOCUMENTS

| | | | |
|---|---|---|---|
| 3,403,080 | 9/1968 | Clay | 526/68 |
| 3,644,583 | 2/1972 | Scoggin | 260/878 B |
| 3,654,094 | 4/1972 | Yamagishi et al. | 203/77 |

*Primary Examiner*—Alan Holler

[57] ABSTRACT

A stream containing at least one noncondensible, under ordinary pressure and temperature, component and at least two components which are condensible under ordinary pressure and temperature are separated by subjecting said stream to successive fractional distillation conditions to successively remove highest boiling components. An overhead produced in one fractional distillation zone is introduced as a feed into the next fractional distillation zone. The penultimate overhead comprising only the noncondensible and a lowest boiling condensible component is partially condensed. The liquid phase is introduced onto the top tray of a last fractionation zone and the vapor phase is introduced below the top tray. A vapor stream containing a single condensible component and at least one noncondensible can be separated in the same manner as the penultimate overhead of a multi-component mixture. The method of this invention can be utilized for separation of hydrogen from a mixture of unreacted propylene and ethylene in a copolymerization reaction.

10 Claims, 1 Drawing Figure

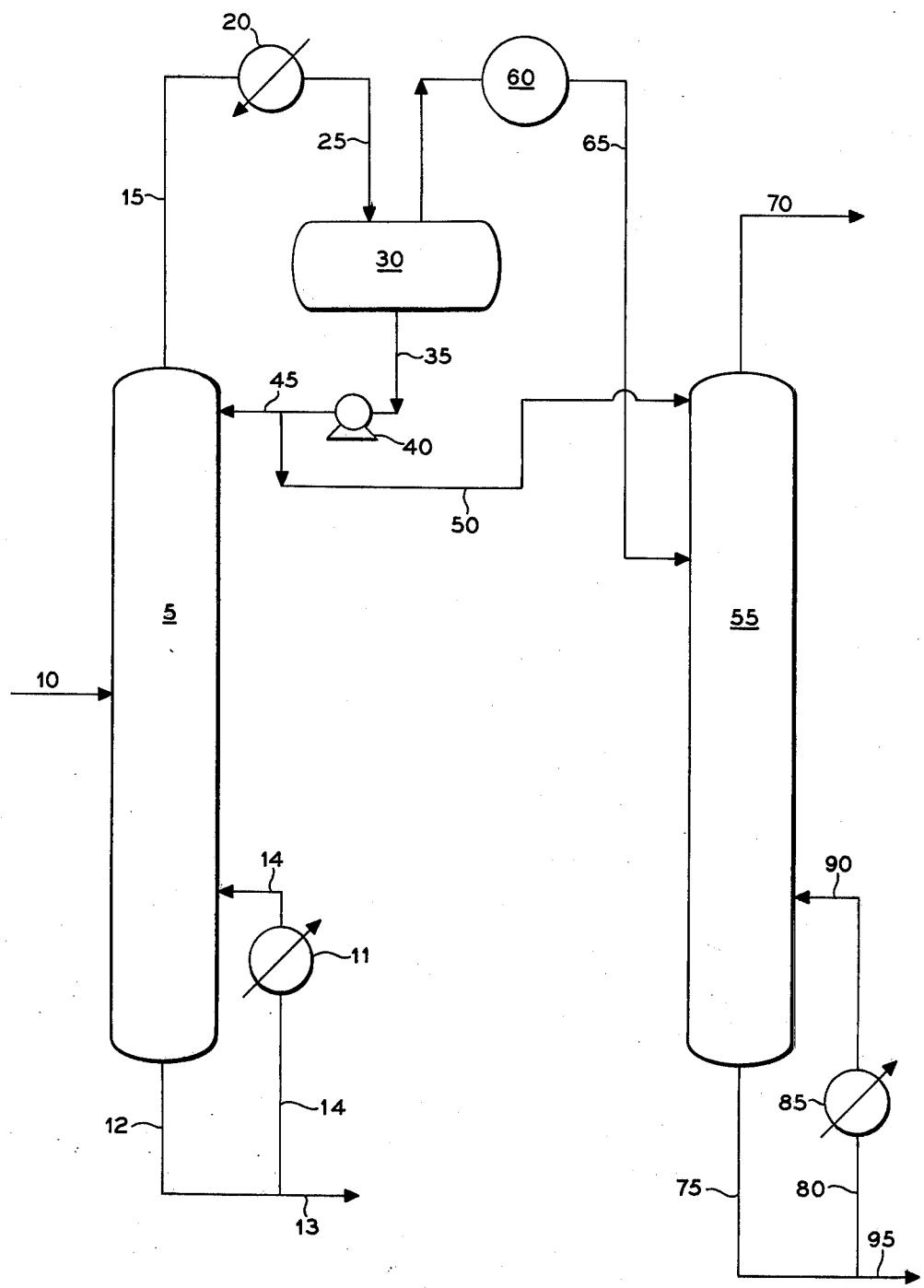

SEPARATION PROCESS

BACKGROUND OF THE INVENTION

This invention relates to an improved separation of a multi-component mixture containing a noncondensible (under ordinary temperature and pressure) component and at least one condensible (under ordinary temperature and pressure) component. In particular, it relates to the separation utilizing fractional distillation.

In chemical processes, it is often necessary to separate a mixture containing noncondensible and condensible components. "Condensible" throughout this specification shall mean capable of being condensed under normally available plant conditions. An example of a mixture which can be separated using the method of the present invention is a mixture of hydrogen, propylene and ethylene. Such mixture has to be separated, for example, in a process of copolymerization of propylene and ethylene. In that process, it is desirable to use in the reaction zone small amounts of hydrogen. The presence of hydrogen in a narrowly defined concentration leads to an improved catalyst productivity and allows improved control of flexural modulus of a copolymer produced in the reaction. In most copolymerization processes, unreacted ethylene and propylene are separated from the copolymer and each other and recycled to the reaction zone. Some of the hydrogen is dissipated in the process; consequently, in order to maintain a narrowly defined concentration thereof in the reaction zone it is necessary to remove all hydrogen from the reagents recycled to the reaction zone and monitor the concentration of hydrogen by introduction of fresh carefully measured amount of hydrogen with each batch, or at a predetermined rate in a continuous process. Different methods of removal of hydrogen from recycle monomer stream are disclosed, for example, in U.S. Pat. Nos. 3,644,583 and 2,900,326.

The present invention provides an improved method for separation of a stream containing at least one of each condensible and noncondensible components.

Thus, one object of this invention is to provide an improved process for separation of a stream containing at least one condensible and one noncondensible component.

Another object of the invention is to provide for an efficient separation of a stream containing hydrogen, propylene and ethylene.

Still another object of the invention is to provide an improved process for catalytic copolymerization of ethylene and propylene in the presence of hydrogen.

A further object of the invention is to provide a method for the removal of hydrogen from an unreacted propylene-ethylene monomer stream and separation of said monomers, which uses a minimum amount of energy and equipment.

A still further object of the invention is to provide a method for separation of hydrogen, unreacted propylene and unreacted ethylene, which eliminates the need for an overhead condenser or any other heat exchanger in the fractionation column used for separation of hydrogen from ethylene.

Other objects of the invention will become apparent to those skilled in the art upon studying this disclosure.

SUMMARY OF THE INVENTION

In accordance with one aspect of the invention, a stream containing at least one noncondensible component and at least two condensible components is separated by subjecting said stream to successive fractional distillation conditions to successively remove highest boiling components. An overhead produced in one fractional distillation zone is introduced as a feed into the next distillation zone, which is operated at a higher pressure than the first zone. The penultimate overhead comprising primarily the noncondensible and a lowest boiling condensible components is partially condensed. The liquid phase is pumped onto the top tray of a last fractionation zone and vapor phase is compressed and introduced below the top tray. The noncondensible component (or components) is then withdrawn as overhead and the condensible component as bottoms.

In accordance with another aspect of the invention, a vapor stream containing a condensible and at least one noncondensible component is partially condensed. The liquid phase is introduced onto the top tray of a fractionation zone and the vapor phase is introduced onto a tray below the top tray. The conditions in the fractionation zone are such as to separate the feed into a bottoms comprising essentially condensible component and an overhead comprising mainly noncondensible component.

In accordance with a further aspect of the invention, a stream comprising hydrogen, propylene and ethylene is separated in a first fractionation zone into an overhead comprising essentially hydrogen and ethylene and a bottoms comprising essentially propylene. The overhead is condensed and the liquid phase thereof is pumped onto the top tray of the second fractionation zone which is maintained at higher pressure than that of the first fractionation zone. The vapor phase is compressed and introduced into the second fractionation zone below the point of introduction of the liquid phase. The conditions in the second fractionation zone, including temperature and pressure, are such as to separate the feed into an overhead comprising mainly hydrogen and bottoms comprising essentially ethylene.

In accordance with still another aspect of the invention, a stream from a copolymerization reaction zone comprising hydrogen, unreacted ethylene, and unreacted propylene is passed to a first fractionation zone and therein subjected to such conditions including temperature and pressure as to separate it into an overhead comprising mainly hydrogen and ethylene and a bottoms comprising essentially propylene. The bottoms is recycled to the copolymerization reaction zone. The overhead is partially condensed and the phases are allowed to separate. The liquid phase is pumped onto the top tray of the second fractionation zone, which is maintained at a higher pressure than the first fractionation zone. Therein the vapor phase is compressed and introduced at a point below that tray. The second fractionation zone is maintained at such distillation conditions including temperature and pressure as to separate the materials introduced therein into a second overhead comprising mainly hydrogen and a second bottoms comprising essentially ethylene. The ethylene stream is recycled to the reaction zone and hydrogen is removed from the system.

Other aspects of the invention will become apparent to those skilled in the art upon studying this specification and the appended claims.

BRIEF DESCRIPTION OF THE DRAWING

The FIGURE depicts a schematic diagram of a portion of a process for production of copolymers to which this invention is applicable.

DETAILED DESCRIPTION OF THE INVENTION

A vapor stream containing condensible and noncondensible components is partially condensed and the vapor and liquid phases are allowed to separate. Then the liquid phase is introduced onto the top tray of a fractionation zone. The vapor phase is compressed and then introduced into the fractionation zone far enough below the top tray to provide the desired stripping of noncondensibles from the liquid phase, while simultaneously providing sufficient absorption stages to effect recovery of condensible components from the vapor phase. It is generally preferred to introduce the vapor phase in the upper half of the fractionation zone.

This invention is applicable to a multi-stage removal of condensible components from a mixture comprising at least one noncondensible and at least one condensible component. The mixture is fed to a first fractionation zone, wherein operating conditions cause separation of the mixture into an overhead comprising mainly lower boiling condensible components and noncondensible components, and into bottoms comprising the highest boiling condensible component. The overhead, from the first fractionation zone, is fed to a subsequent fractionation zone where the next highest boiling condensible component is removed as bottoms and the overhead from that fractionation zone is introduced into yet another fractionation zone. The number of fractionation zones is such as to produce, in the penultimate fractionation zone, an overhead which comprises noncondensible components and only one condensible component. The overhead from the penultimate fractionation zone is partially condensed. The liquid from the condenser is introduced onto the top tray of the last fractionation zone and the vapor is compressed and then introduced at a point below the top tray. The last fractionation zone is operated at a higher pressure than the penultimate fractionation zone so that the saturated liquid, which enters the top stage, is in a subcooled state therein. The subcooled liquid provides internal reflux which serves to scrub and condense the lower boiling component from the compressed vapor feed. Simultaneously, the vapor feed, which enters the last fractionation zone in a super-heated state by virtue of the heat of compression, serves to strip gases from the liquid feed.

This invention is particularly applicable to a process for removal of hydrogen from a stream comprising ethylene, propylene and hydrogen. It can be applied to any process in which removal of hydrogen from a stream comprising hydrogen, ethylene and propylene is desired. One application of the invention is to a catalytic copolymerization of ethylene and propylene. Hydrogen is efficiently removed from a stream leaving a copolymerization reaction zone comprising hydrogen and unreacted ethylene and propylene by passing said stream through a first fractionation zone to remove the propylene as bottoms. The removed propylene is recycled to the polymerization and copolymerization zones. Ethylene and hydrogen are withdrawn as an overhead stream and partially condensed. The phases are allowed to separate in a settling zone. The liquid phase is introduced at the top of the second fractionation zone and the vapor phase is compressed and then fed into the same zone below the top tray. The materials introduced into the second fractionation zone are separated into overhead comprising mainly hydrogen and bottoms comprising essentially ethylene. The substantially hydrogen-free ethylene is then withdrawn as a bottoms stream and recycled to the copolymerization zone.

This invention is applicable to any copolymerization process in which hydrogen is separated from the unreacted ethylene and propylene prior to recycling these to the reaction zone. It is especially applicable to copolymerization of ethylene and propylene described in U.S. Pat. Nos. 3,644,583, 3,358,056, and 3,345,431.

Referring now to the specific embodiment depicted in the FIGURE unconverted liquid monomer stream, from an ethylene-propylene copolymerization reaction zone (not shown), is introduced into a first fractionator 5 via 10. The composition of this stream and its temperature varies depending on the specific copolymerization process employed. Usually, however, stream 10 is a liquid containing hydrogen, unreacted ethylene, and propylene and impurities such as nitrogen and paraffins. The distillation conditions in the first fractionating zone including temperature and pressure are such as to separate stream 10 introduced therein into a first overhead comprising mainly ethylene and hydrogen and a first bottoms comprising mainly propylene.

Although the pressure in the first fractionation zone can vary over a wide range, it is desirable to choose a pressure which is high enough to permit a single stage conventional refrigeration of the overhead. Usually, pressure above about 280 psia (1.93 MPa) is required. The upper limit for the pressure inside the first fractionation zone is governed by economic considerations. The higher the pressure, the more difficult it is to make the separation; therefore, a fractionation zone with higher number of trays is required. The upper limit on the preferred pressure range is about 450 psia (3.10 MPa).

The temperature at the bottom of the first fractionation zone depends on the relative amounts of propylene and ethylene introduced and the pressure selected, but usually it is in the range from about 120° F (49° C) to about 170° F (77° C). The heat necessary to maintain the desired temperature is supplied by reboiler 11. The temperature at the top of the first fractionation zone depends on the choice of bottom temperature and the composition of the stream 10, but is usually between 40° F (4° C) and 70° F (21° C).

The first bottoms is withdrawn from the first fractionation zone 5 as a bottoms stream via 12 and recycled to the polymerization and/or copolymerization reaction zones (not shown) via 13. A portion of the bottom 12 is introduced into reboiler 11 via 14, heated there and returned to the first fractionator 5. The first overhead withdrawn by 15 is passed to a conventional cooler 20 wherein it is partially condensed and passed by 25 to an accumulator 30. In the accumulator 30 the partially liquified overhead stream is permitted to separate into a vapor and a liquid phase. One portion of the liquid phase withdrawn by 35 is passed by a pump 40 and line 45 as reflux to the first fractionation zone. The second portion of said liquid phase is passed from the accumulator 30 via 35, pump 40, and line 50 to the top of a second fractionation zone 55. The relative amounts of streams 45 and 50 depend on the operating conditions in the first fractionation zone, but usually the weight ratio of stream 45 to 50 is from about 1.5 to about 5.5.

The vapor phase from the accumulator 30 is passed to a compressor 60 and therein it is compressed to a pressure sufficient to allow its entry into the second fractionation zone 55. Thus, the minimum pressure depends on the pressure selected for the second fractionation zone 55 and the pressure drop between the compressor 60 and the second fractionation zone 55. The second fractionator is operated at a significantly higher pressure than the first. Consequently, the liquid stream, being in a saturated condition upon leaving accumulator 30 via line 35, is in a subcooled state upon passing pump 40 via line 50 to enter column 55 at the higher pressure. It is partly for this reason that column 55 requires no external reflux since some incremental internal reflux is generated in column 55 by the subcooled feed entering on the top tray. The internal reflux in the top of the column serves to scrub and condense lower boiling components from the compressed vapor feed entering column 55 at a lower point in the column via line 65.

From the compressor 60, the vapor phase is passed by 65 to the second fractionation zone 55 and introduced therein, preferably in the upper half of said second fractionation zone, below the top tray. The vapor feed, which enters in a super-heated state by virtue of the heat of compression induced by compressor 60, serves to strip gases from the liquid feed. Introduction of vapor at this location assures presence of stripping vapor on the top trays, thus minimizing the energy requirements. The conditions in the second fractionation zone including temperature and pressure are such as to separate the materials introduced therein via 50 and 65 into a second overhead comprising mainly hydrogen and a second bottoms comprising essentially ethylene. Both the temperature and the pressure can vary over a wide range; however, it is preferred that the pressure does not exceed 742 psia (5.11 MPa), the critical pressure for ethylene. As the critical pressure is approached, the latent heat of vaporization approaches zero requiring the fractionation zone to have a large diameter to avoid flooding. The minimum preferred pressure is about 475 psia, the pressure required to conveniently retain ethylene in the liquid phase. The corresponding preferred temperature range is about 45 to about 52° F (7°–11° C) at the bottom of the second fractionation zone 55 and about −15° to about −30° F (−25° – −34° C) at the top of the second fractionation zone 55. These conditions, particularly at the bottom of the column, may vary depending on the degree of separation of ethylene and propylene which is effected in first fractionator 5.

The second overhead is withdrawn from the second fractionation zone and removed from the system by 70. A portion of the second bottoms withdrawn by 75 and 80 is heated in reboiler 85 and then returned via 90 near the bottom of the second fractionation zone 55. The vapor generated by the reboiler 85 provides stripping in the column below the point of introduction of vapor feed. The other portion of the stream 75 is recycled via 95 to the copolymerization reaction zone. The relative amounts of streams 95 and 80 vary depending on the operating conditions of the second fractionation zone, but usually the weight ratio of streams 90 to 95 ranges from about 2 to about 10.

EXAMPLE

The following material balance was calculated for a system depicted in the FIGURE and operated at conditions shown below.

| 5/27 MATERIAL BALANCE, MOLS PER DAY Stream Number (see the FIG.) | | | | | | |
|---|---|---|---|---|---|---|
| | 10 | 50 | 65 | 12 | 70 | 95 |
| Hydrogen | 62.9 | 11.6 | 51.3 | — | 62.7 | 0.2 |
| Nitrogen | 35.9 | 13.0 | 22.9 | — | 22.3 | 13.6 |
| Ethylene | 1,135.4 | 1,025.3 | 106.2 | 3.9 | 58.7 | 1,072.8 |
| Ethane | 180.9 | 115.1 | 7.4 | 58.4 | 4.1 | 118.4 |
| Propylene | 9,306.8 | 478.8 | 7.9 | 8,820.1 | 4.8 | 481.9 |
| Propane | 1,282.6 | 34.1 | 0.5 | 1,248.0 | 0.3 | 34.3 |
| TOTALS | 12,004.5 | 1,677.9 | 196.2 | 10,130.4 | 152.9 | 1,721.2 |

Operating Conditions:
First Fractionation Zone (5)
Bottom Temperature          127° F (53° C)
Top Temperature             52° F (11° C)
Pressure                    304 psia (2.10 MPa)
Accumulator (30)
Temperature                 −30° F (−34° C)
Pressure                    290 psia (2.00 MPa)
Second Fractionation Zone (55)
Bottom Temperature          48° F (9° C)
Top Temperature             −25° F (−32° C)
Pressure                    500 psia (3.45 MPa)

Many modifications of this invention will become apparent to those skilled in the art upon studying this disclosure. For example, if the condensible components in the stream which is sought to be separated have close boiling points or form azeotropic mixtures, simple fractional distillation can be replaced by extractive distillation. Also, those skilled in the art will recognize that "trays", as used throughout this specification, include not only a variety of plates of varying designs utilized to increase the efficiency of separation, but also different types of packing included for the same purpose. In the latter case, the expression "trays" is equivalent to equilibrium stages. It should also be noted that if, in some applications, two or more condensible components need not be separated from each other or one another, these can be treated as one component for the purpose of applying this invention. All changes and modifications that fall within the spirit of this invention are intended to be included within its scope.

I claim:
1. A process for separation of a vapor stream containing a condensible component and at least one noncondensible component which comprises:
   (a) condensing a portion of said vapor stream and allowing said stream to separate into a vapor phase and a liquid phase;
   (b) introducing said liquid phase onto the top tray of a fractionation zone;
   (c) compressing said vapor phase to a pressure sufficient to permit its entry into the fractionation zone and introducing same into said fractionation zone, below the point of introduction of said liquid phase and subjecting said liquid phase and vapor phase therein to such distillation conditions including temperature and pressure as to cause a separation of said phases into an overhead comprising mainly said noncondensible component and said bottoms comprising essentially said condensible component.

2. A process for separation of a stream containing at least two condensible and at least one noncondensible components which comprises:
   (a) introducing said stream to successive fractionation zone, each operated at such distillation conditions including temperature and pressure as to separate a feed introduced therein into a bottoms comprising mainly a highest boiling condensible component of the feed and an overhead comprising mainly the remaining condensible and the noncondensible, the overhead from the first fractionation zone serving as a feed for the next fractionation zone so that a penultimate overhead comprises essentially one condensible and all noncondensible components;

(b) condensing a part of said penultimate overhead and allowing said overhead to separate into a vapor phase and a liquid phase;

(c) introducing said liquid phase onto the top tray of a final fractionation zone; and (d) compressing said vapor phase to a pressure sufficient to permit its entry into the final fractionation zone and introducing same into said final fractionation zone below the point of introduction of said liquid phase and subjecting said liquid and vapor phase therein to such distillation conditions including temperature and pressure as to cause a separation of said phases into a final overhead comprising mainly noncondensible components and a final bottoms comprising essentially the lowest boiling condensible component.

3. A process as claimed in claim 2 wherein the noncondensible component is hydrogen, the highest boiling condensible is propylene and the lowest boiling condensible is ethylene.

4. A process for removal of hydrogen from a stream comprising hydrogen and unreacted ethylene and propylene, said stream leaving a copolymerization reaction zone which comprises:

(a) introducing said stream into a first fractionation zone and therein maintaining such distillation conditions including temperature and pressure as to separate said stream into a first overhead comprising mainly hydrogen and ethylene and a first bottoms comprising essentially propylene;

(b) cooling in a cooling zone said first overhead to a temperature sufficient to liquify a portion thereof and allowing separation of cooled first overhead stream into a vapor phase and a liquid phase;

(c) introducing the liquid phase onto the top tray of a second fractionation zone;

(d) compressing the vapor phase to a pressure sufficient to allow introduction thereof into the second fractionation zone and feeding said compressed vapor phase into said second fractionation zone below the point of introduction of said liquid phase;

(e) subjecting liquid phase and compressed vapor phase introduced into the second fractionation zone to such distillation conditions therein including temperature and pressure as to cause a separation of said phases into a second overhead comprising mainly hydrogen and a second bottoms comprising essentially ethylene; and (f) recycling said second bottoms to said copolymerization reaction zone.

5. A process as claimed in claim 4 further comprising:
recycling a part of the liquid separated in step (c) to the top of the first fractionation zone;
subdividing the second bottoms stream into a product stream and a recycle stream;
heating said recycle stream to provide reboiling heat; and
introducing hot recycle stream near the bottom of the second fractionation zone.

6. A process as claimed in claim 2 wherein the pressure in said first fractionation zone is in the range from about 280 psia to about 450 psia (1.93 to 3.10 MPa), the temperature at the bottom of said first fractionation zone is in the range from about 120° F (49° C) to about 170° F (77° C), the temperature at the top of said first fractionation zone is in the range from about 40° F (4° C) to about 70° F (21° C), the pressure in said second fractionation zone is in the range from about 475 psia to about 625 psia (3.28 to 4.31 MPa), the temperature at the bottom of said second fractionation zone is in the range from about 45° F (7° C) to about 52° F (11° C), and in the range from about −15° to about −30° F (−25° − −34° C) to the top of the second fractionation zone.

7. In a process for block copolymerization of propylene and ethylene in the presence of a catalyst and a narrowly defined amount of hydrogen, hydrogen being used in a reaction zone to improve catalyst productivity and to control flexural modulus of the block copolymer produced including the steps of forming a block copolymer in a reaction zone, separating the block copolymer from unreacted monomers of propylene and ethylene and hydrogen and recycling the unreacted monomers to the reaction zone the improvement which comprises:

(a) passing unreacted monomers and hydrogen to a first fractionation zone and therein subjecting said unreacted monomers and hydrogen in said first fractionation zone to such distillation conditions including temperature and pressure as to separate these into a first overhead comprising mainly ethylene and hydrogen and a first bottoms comprising essentially propylene;

(b) recycling the first bottoms propylene stream to the reaction zone;

(c) cooling said first overhead stream to a temperature sufficient to condense a portion thereof and allowing separation of cooled first overhead stream into a vapor phase and a liquid phase;

(d) introducing said liquid phase at the top of a second fractionation zone;

(e) compressing said vapor phase to a pressure sufficient to allow its entry into the second fractionation zone and feeding said compressed vapor phase into the second fractionation zone below the point of introduction of the liquid phase;

(f) maintaining such distillation condition in said second fractionation zone including temperature and pressure as to separate the pressurized vapor phase and the liquid phase fed therein into a second overhead comprising mainly hydrogen and second bottoms comprising essentially ethylene; and (g) recycling said second bottoms to the reaction zone.

8. A process as claimed in claim 1 wherein the vapor phase is introduced in the upper half of the fractionation zone.

9. A process as claimed in claim 2 wherein the vapor phase is introduced in the upper half of the final fractionation zone and wherein the pressure maintained in the final fractionation zone is significantly higher than that maintained in the penultimate fractionation zone.

10. A process as claimed in claim 4 wherein the vapor phase is introduced in the upper half of the second fractionation zone and the pressure in said second fractionation zone is significantly higher than that of the first fractionation zone.

* * * * *

UNITED STATES PATENT AND TRADEMARK OFFICE
CERTIFICATE OF CORRECTION

PATENT NO. : 4,075,287
DATED : February 21, 1978
INVENTOR(S) : Jack S. Scoggin

It is certified that error appears in the above-identified patent and that said Letters Patent are hereby corrected as shown below:

Column 6, line 64, "zone" should be --- zones ---.

Column 7, line 1, after "noncondensible" insert --- components ---.

Column 8, line 12, "to" should be --- at ---.

Signed and Sealed this

Eighth Day of August 1978

[SEAL]

Attest:

RUTH C. MASON
Attesting Officer

DONALD W. BANNER
Commissioner of Patents and Trademarks